US005314887A

United States Patent [19]

Aldrich et al.

[11] Patent Number: 5,314,887

[45] Date of Patent: May 24, 1994

[54] 2-AMINO-1, 4-DIHYDROPYRIDINE DERIVATIVES WITH CALCIUM AGONIST AND ALPHLAL-ANTAGONIST ACTIVITY

[75] Inventors: Paul E. Aldrich; Richard A. Earl, both of Wilmington, Del.; Philip Ma, Chadds Ford, Pa.

[73] Assignee: The Du Pont Merck Pharmaceutical Company, Wilmington, Del.

[21] Appl. No.: 968,933

[22] Filed: Oct. 30, 1992

Related U.S. Application Data

[62] Division of Ser. No. 549,820, Jul. 9, 1990, Pat. No. 5,166,148.

[51] Int. Cl.[5] .................. A61K 31/505; C07D 401/14; C07D 403/14

[52] U.S. Cl. ................................ 514/252; 514/235.8; 544/121; 544/212; 544/234; 544/295; 544/333; 544/357; 544/360; 544/362; 544/364; 544/365; 546/116; 546/256; 546/258; 546/283; 546/310

[58] Field of Search ...................... 544/295, 121, 360; 514/235.8, 252

[56] References Cited

U.S. PATENT DOCUMENTS 5,166,147 11/1992 Earl .................................... 544/295

*Primary Examiner*—C. Warren Ivy
*Assistant Examiner*—James H. Turnipseed
*Attorney, Agent, or Firm*—Gildo E. Fato

[57] ABSTRACT

There are provided novel 1,4-dihydropyridine compounds possessing both calcium agonist and $alpha_1$-antagonist activity useful for treating congestive heart failure, pharmaceutical compositions containing them and methods of using these compounds to treat congestive heart failure in a mammal.

12 Claims, No Drawings

2-AMINO-1, 4-DIHYDROPYRIDINE DERIVATIVES WITH CALCIUM AGONIST AND ALPHLAL-ANTAGONIST ACTIVITY

This is a division of application Ser. No. 07/549,820, filed Jul. 9, 1990, now U.S. Pat. No. 5,166,148.

FIELD OF THE INVENTION

This invention relates to novel 1,4-dihydropyridines, pharmaceutical compositions containing them and methods of using them to treat congestive heart failure, and more particularly to such 1,4-dihydropyridines which combine both calcium agonist and alpha$_1$-antagonist activity and are useful in the treatment of congestive heart failure.

BACKGROUND OF THE INVENTION

Over the past decade, dihydropyridine calcium antagonists or calcium channel blockers have become widely known therapeutic agents having vasodilator properties which can be used as antihypertensives and coronary dilator agents. These compounds inhibit the entry of calcium into cells, or its mobilization from intracellular stores. More recently, it has been found that small structural modifications of these known compounds produce dihydropyridines with effects diametrically opposed to those of the calcium channel blockers. Dihydropyridines such as Bay K8644 and CGP 28392 (FIG. 1) promote an influx of calcium ions into cells, thereby producing positive inotropic and vasoconstrictor effects. Bay K8644 is more than ten times as potent as CGP 28392 as a calcium agonist. However, Bay K8644 is not useful as a cardiotonic because of its coronary vasoconstricting properties. Therefore it is only useful as a pharmacological tool to ascertain the function of calcium entry blockers.

FIG. 1

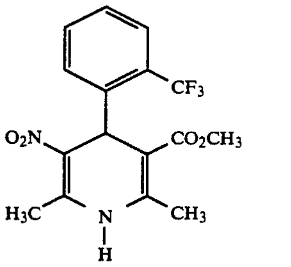

Bay K8644

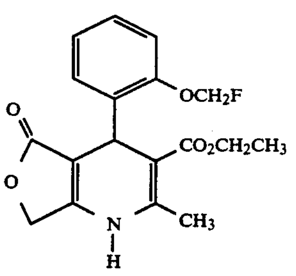

CGP 28392

Representative of the art in the field of dihydropyridine calcium agonists are U.S. Pat. No. 4,248,873 (Bossert et al.), issued Feb. 3, 1981; European Patent Application 0071819 published Feb. 16, 1983 by Boshagen et al.; and U.S. Pat. No. 4,537,881 (Franckowiak et al.), issued Aug. 27, 1985. Literature references include M. Schram, et al., *Nature* 303:535 (1983); M. Schram, et al., *Arzneium-Forsch,* 33:1268 (1983); P. Erne, et al., *Biochem. Biophys. Res. Commun.* 118:482 (1984). Dihydropyridine calcium agonists which contain an amino group in the 2-position are described in U.S. Pat. No. 4,532,248 (Boshagen et al.), issued Jul. 30, 1985.

Combining calcium agonist properties and alpha$_1$-adrenergic blocking properties in a single molecular structure provides a new and attractive approach for the treatment of congestive heart failure. The combination of these two types of activities affords a novel class of cardiotonics which have cardiac stimulatory effects in combination with pronounced vasodilator properties. The detrimental vasoconstricting properties which are normally associated with dihydropyridine calcium agonists are minimized by the alpha$_1$-adrenergic blocking properties which cause dilation of the peripheral vasculature. Applicants are not aware of any references that describe this combination of properties in a single compound, other than co-assigned U.S. Pat. No. 4,868,181 (Johnson et al.) issued Sep. 19, 1989.

SUMMARY OF THE INVENTION

According to the present invention there are provided novel 1,4-dihydropyridine derivatives of the general formula (I) which possess both calcium channel promoting activity and alpha$_1$-adrenergic blocking properties and are useful in the treatment of congestive heart failure. These compounds have the formula:

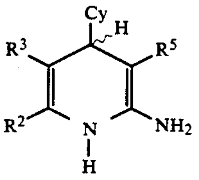

(I)

or a pharmaceutically acceptable salt thereof wherein:

$R^2$ is alkyl of 1–4 carbon atoms, CN, $CH_2OH$, $CH_2OCH_2CH_2NH_2$ or $NH_2$;

$R^3$ is $NO_2$, H, CN, $CONH_2$, or $R^2$ and $R^3$ taken together are:

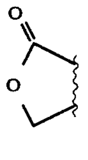

or

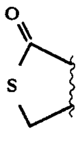

;

Cy, when $R^5$ is CHO, $CO_2CH_2CHOHC_6H_5$, $CO_2CH(OCH_3)C_6H_5$, $NO_2$, $CONHC_6H_5$, or $CO_2$ alkyl of 1–10 carbon atoms, is a cyclic group selected from the group:

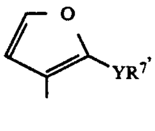

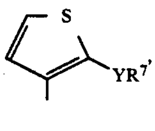

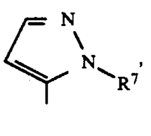

-continued

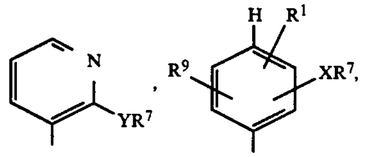

,

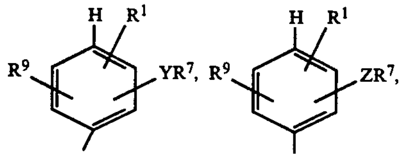

,

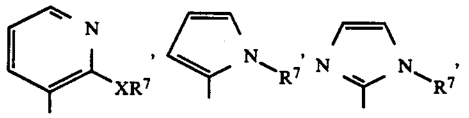

, , ,

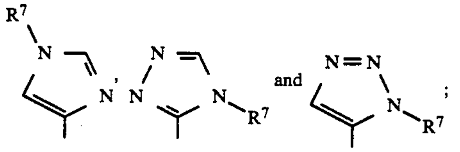

, and ;

$R^1$ and $R^9$ independently are H, alkyl of 1–4 carbon atoms, haloalkyl of 1–4 carbon atoms, alkoxy of 1–10 carbon atoms, halogen, or $NO_2$;

Cy, when $R^5$ is $COR^7$, $CO_2R^7$ or $CONHR^7$ is phenyl optionally substituted with one or two substituents independently selected from the group consisting of: alkyl of 1–4 carbon atoms, haloalkyl of 1–4 carbon atoms, alkoxy of 1–4 carbon atoms, thioalkyl of 1–4 carbon atoms, alkylsulfinyl of 1–4 carbon atoms, alkylsulfonyl of 1–4 carbon atoms, halogen, or $NO_2$, or Cy is 2-, 3-, or 4-pyridinyl, 2- or 3-furanyl, 2- or 3-thienyl, 2-, 4-, or 5-thiazolyl, 2-, 4-, or 5-pyrimidinyl, or

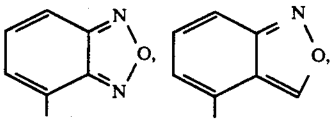

,

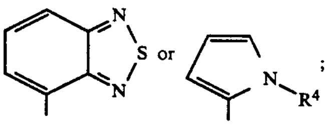

or ;

X is $NR^4$, O, S, SO, $SO_2$, N→O;

Y is $CH_2$,

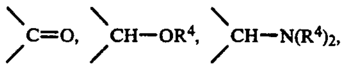

, , ,

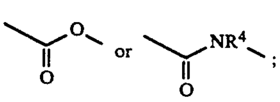

or ;

-continued

Z is

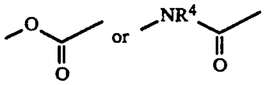

or where $R^4$ is H or an alkyl group of 1–4 carbon atoms;

$R^7$ is

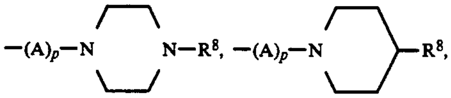

,

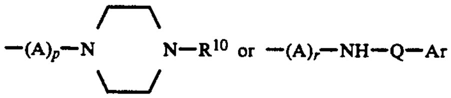

or where

A is a straight or branched alkyl, alkenyl, or alkynyl chain or $-(CH_2)_nCHOHCH_2-$;

$R^{10}$ is

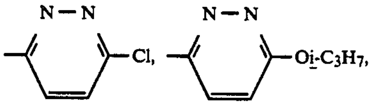

,

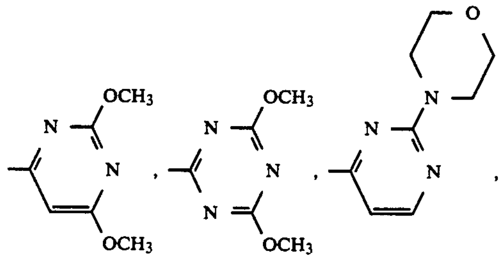

, , ,

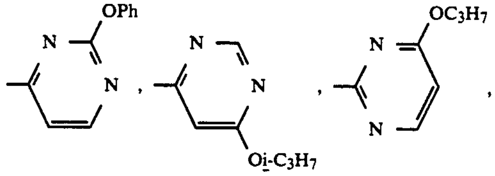

, , ,

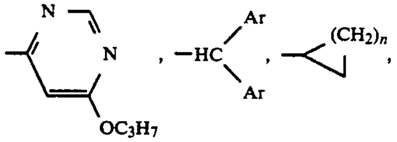

, , ,

2-, 3-, or 4-pyridinyl, 2-, or 4-pyrimidinyl, or 2-pyrazinyl;

$R^8$ is Ar,

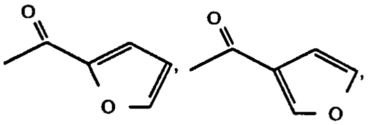

, ,

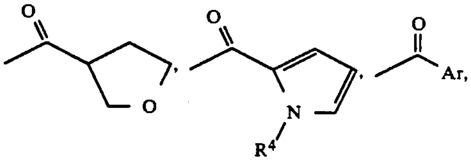

, ,

-continued

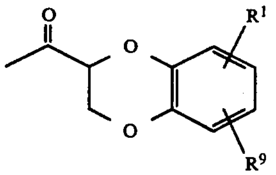

where

Ar is phenyl optionally substituted with one or two substituents independently selected from the group consisting of: alkyl of 1–4 carbon atoms, haloalkyl of 1–4 carbon atoms, alkoxy of 1–4 atoms, halogen, or $NO_2$;

Q is $(CH_2)_q$, $(CH_2)_nO$, $(CH_2)_nNH$ or $(CH_2)_nS$;

n is independently 1 to 4;

p is 2 to 10;

q is 0 to 2; and r is 1 to 10.

The compounds of the present invention can exist as optical isomers and both the racemates as well as the individual optical isomer which confers agonist activity are within the scope of the present invention. The racemic mixtures can be separated into their individual isomers by well known techniques such as the separation of the diastereomeric salts formed with optically active acids, followed by conversion back to the optically active 1,4-dihydropyridine.

Also provided are pharmaceutical compositions comprising a suitable pharmaceutical carrier and compound of formula (I) and methods of using the compounds of formula (I) to treat congestive heart failure.

PREFERRED EMBODIMENTS

Preferred compounds are those compounds of formula (I) where:

$R^2$ is $CH_3$; and/or $R^3$ is $NO_2$; and/or

Cy is

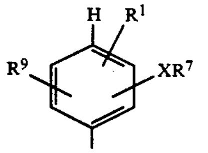

and $R^5$ is an alkyl ester of 1–4 carbon atoms; where $R^1$ and $R^9$ are H; and/or X is O, S, SO, or $SO_2$; and/or

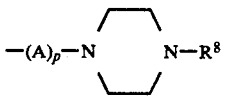 or 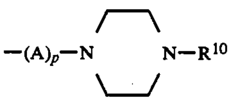

$R^7$ is:

where

A is $-(CH_2)p-$ where p is 2 to 5; and/or $R^8$ is Ar or

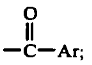

where

Ar is phenyl optionally monosubstituted with $OCH_3$, $CH_3$, or Cl; and/or $R^{10}$ is 2- or 4-pyrimidinyl.

SPECIFICALLY PREFERRED COMPOUNDS (a) 2-Amino-1,4-dihydro-4-(2-{5-[4-(2-pyrimidinyl)-1-piperazinyl]-pentyloxy}phenyl)-6-methyl-5-nitro-3-pyridinecarboxylic acid methyl ester (b) 2-Amino-1,4-dihydro-4-(2-{5-[4-(2-methoxyphenyl)-1-piperazinyl]-pentyloxy}phenyl)-6-methyl-5-nitro-3-pyridinecarboxylic acid methyl ester (c) 2-Amino-1,4-dihydro-4-(2-{4-[4-(2-methoxyphenyl)-1-piperazinyl]-butylthio}phenyl)-6-methyl-5-nitro-3-pyridinecarboxylic acid methyl ester (d) 2-Amino-1,4-dihydro-4-(2-{4-[4-(2-methoxyphenyl)-1-piperazinyl]-butylsulfinyl} phenyl)-6-methyl 5-nitro-3-pyridinecarboxylic acid methyl ester (e) 2-Amino-1,4-dihydro-4-(2-{4-[4-(2-methoxyphenyl)-1-piperazinyl]-butylsulfonyl}phenyl)-6-methyl-5-nitro-3-pyridinecarboxylic acid methyl ester (f) 2-Amino-1,4-dihydro-4-(2-{4-[4-(2-pyrimidinyl)-1-piperazinyl]-butylsulfinyl}phenyl)-6-methyl-5-nitro-3-pyridinecarboxylic acid methyl ester (g) 2-Amino-1,4-dihydro-4-(2-{4-[4-(2-methoxyphenyl)-1-piperazinyl]-pentylsulfinyl}phenyl)-6-methyl-5-nitro-3-pyridinecarboxylic acid methyl ester.

DETAILED DESCRIPTION OF THE INVENTION

SYNTHESIS

According to the present invention, the dihydropyridines of the general formula (I) can be prepared by the processes illustrated below. It is understood that in all of these processes $R^1$, $R^2$, $R^3$, $R^4$, $R^5$, $R^7$, $R^8$, $R^9$, $R^{10}$, Ar, X, Y, A, p, r, Q, n, q are as defined above.

Method A

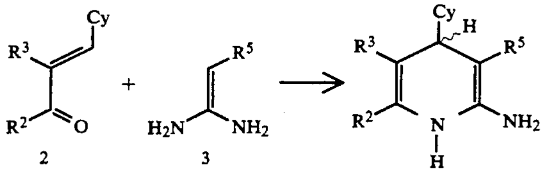

2 3 (I)

This method is carried out using the process described in U.S. Pat. No. 4,772,596, issued Sep. 20, 1988; H. Meyer, et al., *Arzneim.-Forsch.* 31:1173, (1981); K. Meguro, et al., *Chem. Pharm. Bull*, 33:3787 (1987).

The reaction is carried out in a mixture of an equimolar ratio of the starting compounds 2 and 3 in the presence of an alcoholic solvent such as methanol, ethanol i-propanol or n-butanol, an aromatic hydrocarbon such as benzene or toluene, an ether such as tetrahydrofuran (THF) or dioxane, a halogenated hydrocarbon such as chloroform or carbon tetrachloride, an aprotic polar solvent such as acetonitrile, dimethylformamide (DMF) or dimethylsulfoxide (DMSO), or other acceptable solvent at a temperature in the range of room temperature to about 200° C., preferably at about 60°–110° C. Separation of the desired product from the reaction mixture is effected by conventional techniques such as filtration, concentration, extraction, column chromatography, recrystallization, etc.

Method B

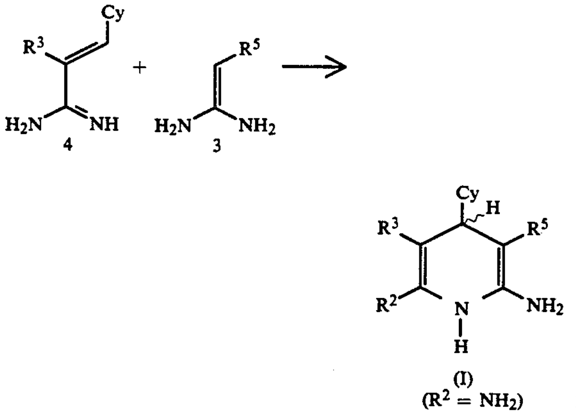

4 3

(I)
($R^2$ = $NH_2$)

This method is carried out using the procedure described by H. Meyer, et al., *Liebigs Ann. Chem.*, 1476 (1978). The reaction is carried out with an equimolar mixture of compounds 3 and 4 in the presence of a solvent such as described in Method A, using the reaction conditions described in Method A.

Compounds of the formula 3 can be prepared by reacting a cyanoacetic acid ester of formula 8 ($NC—CH_2—COO(A)_r—R^{11}$) with ammonia or with an ammonium salt according to a known method [S. A. Glickman, A. C. Cope, *J. Am. Chem. Soc.* 67:1017 (1945); S. M. McElvain, B. E. Tate, *J. Am. Chem. Soc.* 73:2760 (1951)]. Compounds of the formula 8 can be prepared by a conventional esterification between cyanoacetic acid or cyanoacetic acid chloride, and an alcohol of formula 9 ($HO—(A)_r—R^{11}$), where $R^{11}$ is defined as Br, Cl, I, tosylate (OTs), mesylate (OMs), or triflate (OTf).

The compound of formula 3 may be, and preferably is, employed in the form of an acid addition salt, for example a salt with hydrochloric acid or acetic acid. Where such a salt is used, it is preferred that a base, for example an alkali metal alkoxide (such as sodium methoxide or sodium ethoxide) should be added to the reaction mixture, preferably in an equimolar amount.

Compound of the formula 3, where $R^5$ is $NO_2$, has been reported in the literature [H. Mertens, R. Troschutz, *Arch. Pharm.* 319:14 (1986)].

Compounds of the formula 2 may be prepared (Scheme 1) by the dehydrating condensation of an aldehyde 5 with compounds of the formula 6 according to a known method [e.g., G. Jones, "Knoevenagel Condensation" in *Org. Reactions* Vol. 15, 204 (1967)], or the condensation of compounds of the formula 7 with compounds of the formula 6 according to the procedure described by I. Morita, et al., *Chem. Pharm. Bull.* 36:1139 (1988).

Scheme 1

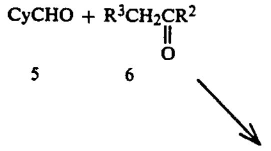

5 6

-continued

Scheme 1

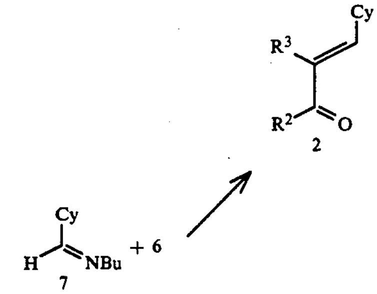

2

7

Compounds of the formula CyCHO (5) are commercially available, or may be prepared by methods described in the literature. The heterocyclic aldehydes used as intermediates are available by methods described in standard works on heterocyclic chemistry such as Katritzky and Rees, *Comprehensive Heterocyclic Chemistry,* Vols. 2-5, Pergamon Press, N.Y., 1984. In some instances, the preparation of the hydroxymethyl compounds are described in the literature. These can be converted to the corresponding aldehydes by known methods, such as oxidation with manganese dioxide, or dimethysulfoxide activated with oxalyl chloride.

Compounds of the formula 13 may be prepared according to Method C. Compound 10 (where X' is $NR^4$, O, or S and $R^{12}$ is $CO_2R^4$ or $CH_2OH$ (or a protected alcohol)) is alkylated with an appropriate connector chain 11 to give compound 12. This reaction is carried out in the presence of an aromatic hydrocarbon such as benzene or toluene, a halogenated hydrocarbon such as dichloromethane or carbon tetrachloride, an ether such as THF or DME, or an aprotic solvent such as acetonitrile or DMF, in the presence of a base such as potassium carbonate, sodium carbonate, sodium bicarbonate, or sodium hydride, at a temperature in the range of about −20° C. to 200° C., preferably of about 25° C. to 150° C. Separation of the desired product from the reaction mixture is effected by conventional operations such as filtration, concentration, extraction, column chromatography or recrystallization.

Method C

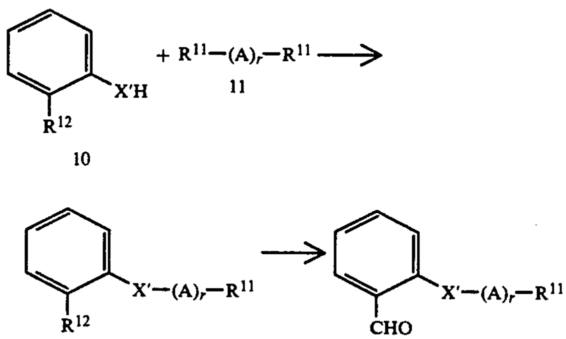

10 11

12 13

Compounds of the formulas 14, 15, 16 and 17 may be purchased commercially, or prepared according to the methods described by S. F. Campbell, et al., *J. Med. Chem.* 30, 49, 999, 1794 (1987), and by other methods reported in the literature.

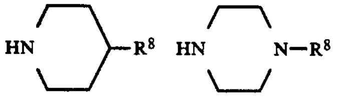

14 15

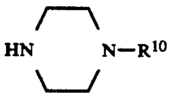

$H_2NQ$—Ar 16 17

Compounds of the formula 21 may be prepared according to Method D. Compound 19 (prepared from 2 and 18) is converted to the carboxylic acid with a fluoride source, such as tetrabutylammonium fluoride or hydrogen fluoride. Treatment with 1,1'-carbonyldiimidazole provides the activated imidazolide 20, which may be reacted with alcohols of the type $R^7OH$ to produce 21.

Method D

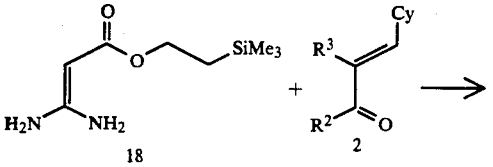

18 2

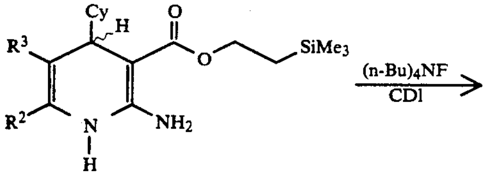

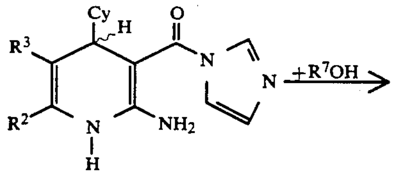

20

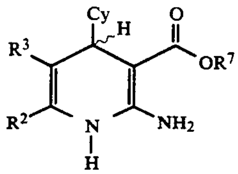

21 [(I), where $R^5$ is $CO_2R^7$]

As shown in Method E, compounds of the formulas 23 and 25 may be prepared by reacting compounds of the formulas 22 and 24 with amines 14 or 15 or 16 or 17, respectively. The reaction is carried out by reacting 22 or 24 with amines 14 or 15 or 16 or 17 in a molar ratio of 1.0:1.0 to 1.0:4.0 in the presence of a base such as potassium carbonate, sodium carbonate, sodium bicarbonate, triethylamine or sodium hydroxide. The reaction is performed in the presence of an alcoholic solvent such as methanol, ethanol, i-propanol or n-butanol, an aromatic hydrocarbon such as benzene or toluene, an ether such as tetrahydrofuran (THF) or dioxane, a halogenated hydrocarbon such as chloroform or carbon tetrachloride, an aprotic polar solvent such as acetonitrile, dimethylformamide (DMF) or dimethylsulfoxide (DMSO), or the like at a temperature in the range of about room temperature to 200° C., preferably at about 25°-110° C. Separation of the desired product from the reaction mixture is effected by conventional techniques such as filtration, concentration, extraction, column chromatography, recrystallization, etc.

This method is also applicable for compounds of the formula 24, where Y or Z is substituted for X.

Method E a)

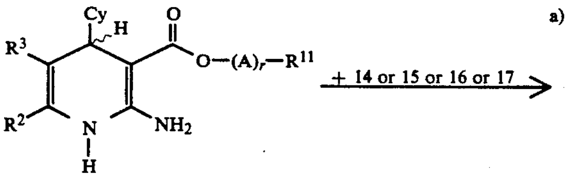

22

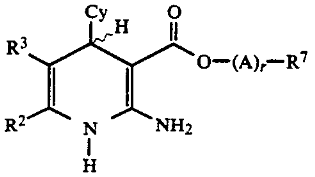

23 [(I), where $R^5$ is $CO_2R^7$]

b)

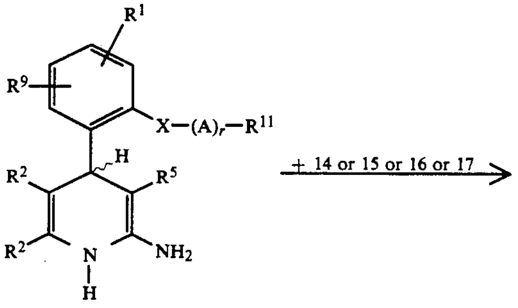

24

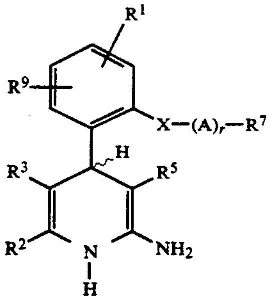

25 where

X is $NR^4$ or S, 25 can be oxidized to $R^4N{\rightarrow}O$ ($N{\rightarrow}O$ means N-oxide) or SO or $SO_2$, respectively, with an oxidizing agent such as hydrogen peroxide, peracetic acid or m-chloroperbenzoic acid.

Compounds of the formula 27, where $R^{12A}$ is S or O, (Method F) may be prepared according to procedures described in the literature, such as I. Sircar, et al., *Tetra-*

*hedron Lett.* 29, 6835 (1988) and U.S. Pat. No. 4,642,310, issued Feb. 10, 1987.

Method F

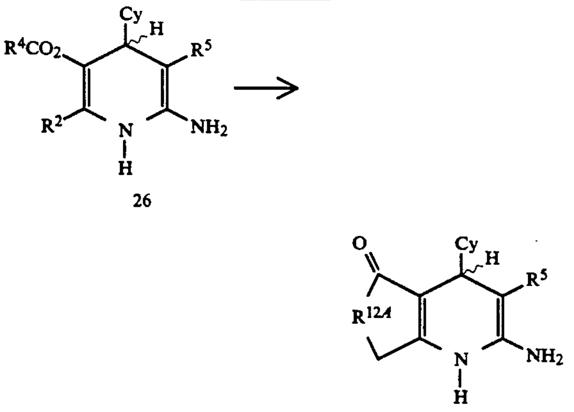

26

27

The above preparation processes are given merely for illustration. The preparation of the compounds of the formula (I) is not limited to these processes, but any modification of these processes can be applied in the same manner to the preparation of the compounds according to the invention.

A resulting basic compound can be converted into a corresponding acid addition salt by reacting it with an inorganic or organic acid as is well known to one skilled in the art. Therapeutically useful acids include, for example, inorganic acids, such as hydrochloric, hydrobromic, sulfuric, phosphoric or nitric acid, or organic acids, such as formic, acetic, propionic, succinic, maleic, fumaric, tartaric or ascorbic acids.

The compounds of this invention and their preparation can be further understood by the following examples, which should not constitute a limitation thereof. In these examples, unless otherwise indicated, all temperatures are in degrees Celsius and parts and percentages are by weight.

EXAMPLE 1

Part A: 2-[(4-Chlorobutyl)thio]benzyl alcohol:

To a 5 liter 4-neck round-bottom flask fitted with mechanical stirrer, thermowell, and addition funnel, under a nitrogen atmosphere, was added 150.0 g of o-mercaptobenzyl alcohol, 2400 ml of isopropanol and 295.72 g of anhydrous potassium carbonate. The reaction mixture was cooled in an ice bath, as 246.6 ml of 1-bromo-4-chlorobutane was added dropwise. After addition was complete, the mixture was allowed to warm to room temperature, and stirred at room temperature overnight. The mixture was filtered through a pad of filter aid, and the solid was rinsed with fresh isopropanol. The solvent was removed by rotary evaporation to give 246.0 g of the product as a brown oil. $^1$H-NMR ($CDCl_3$) δ 1.7–2.1(m,4H); 2.3(br s,1H); 2.85–3.0(t,2H); 3.5–3.6(t,2H); 4.75(s,2H); 7.2–7.4(m,4H).

Part B: 2-[(4-Chlorobutyl)thio]benzaldehyde:

To a 5 liter 4-neck round-bottom flask fitted with mechanical stirrer, thermowell and addition funnel, under a nitrogen atmosphere, was added 78.4 ml of oxalyl chloride and 925 ml of dichloromethane. The reaction was cooled to −78° C. with a dry ice/acetone bath. Then 125.3 ml of distilled dimethylsulfoxide was added dropwise, maintaining the reaction temperature below −65° C. After the addition was complete, 138.4 g of 2-[(4-chlorobutyl)thio]benzyl alcohol was added in 300 ml of dichloromethane. After addition was complete, the mixture was stirred for 30 min., then 417.3 ml of triethylamine was added. The bath was allowed to warm gradually to room temperature and stirred overnight at this temperature. The reaction mixture was poured into a 12 liter flask containing a stirring mixture of 3100 g of crushed ice and 4730 ml of 1N HCl. After stirring for 30 min., the mixture was extracted with dichloromethane (3×300 ml) the organic solution was dried over magnesium sulfate, filtered and concentrated to a brown oil. The product was further purified by column chromatography on silica gel, eluting with 10% ethyl acetate in hexane to give 117.7 g of the pure product as an oil. $^1$H-NMR ($CDCl_3$) δ 1.8–2.0(m,4H); 3.0(t,2H); 3.6(t,2H); 7.2–7.6(m,3H); 7.8(m,1H); 10.4(s,1H).

Part C: N-{2-[4-Chlorobutyl) thiol phenylmethylene}-1-butanamine

To a 4 liter 4-neck round-bottom flask fitted with mechanical stirrer and thermowell, under a nitrogen atmosphere, was added 117.6 g of 2-[(4-chlorobutyl)thio]benzaldehyde and 622 ml of diethyl ether, followed by 395.2 g of magnesium sulfate, 65.81 ml of N-butylamine and 2.63 g of concentrated sulfuric acid (added dropwise). This mixture was stirred at room temperature, overnight. The solid was filtered off, and the filtrate was concentrated to give the imine as an oil, 138.3 g. $^1$H-NMR ($CDCl_3$) δ 1.9(t,3H); 1.3–1.55(m,2H); 1.6–2.0(m,6H); 3.9(t,2H); 3.4–3.6(t,2H); 2.6–2.8(t,2H); 7.2–7.4(m,3H); 7.9(m,1H); 8.8(s,1H).

Part D: 4-{2-[(4-Chlorobutyl)thio]phenyl}-3-nitro-3-buten-2-one

To a 2 liter 4-neck round-bottom flask fitted with mechanical stirrer and thermowell, under a nitrogen atmosphere, was added 138.2 g of N-{2-[(4-chlorobutyl)thio]phenylmethylene}-1-butanamine and 350 ml of benzene, followed by 91.9 ml of acetic anhydride. The mixture was cooled in an ice water bath as 50.18 g of nitroacetone was added. The bath was permitted to warm to room temperature and the reaction stirred overnight. The solvent was removed by rotary evaporation and the product was partitioned between ether and sodium bicarbonate. The organic layer was washed with brine, dried over magnesium sulfate and concentrated to dryness. Purification via column chromatograph on silica gel, eluting with 15% ethyl acetate in hexane provided the product as a pale orange oil. Mass spectrum: 314 (M+1).

Part E: 2-Amino-1,4-dihydro-4-{2-[(4-chlorobutyl)thio]-phenyl}-6-methyl-5-nitro-3-pyridinecarboxylic acid methyl ester To a 1-neck 200 ml round-bottom flask containing 4.7 g of 4-{2-[(4-chlorobutyl)thio]phenyl}-3-nitro-3-buten-2-one and a stir bar, under a nitrogen atmosphere, was added 20 ml of methanol. The solution was cooled in an ice bath as 3.43 g of amidino-acetic acid methyl ester hydrochloride and 5.13 ml of 25% sodium methoxide in methanol was added. An orange solid formed shortly. After 1.5 hr., the product was collected by filtration and washed with cold methanol and dried for 1 hr. under vacuum, to give 4.85 g of the dihydropyridine as an orange solid, m.p. 169°-170° C. $^1$H-NMR ($d_6$-DMSO) δ 1.6-1.95(m,4H); 2.5(s,3H); 2.8-3.0(m,2H); 3.35-3.4(s,3H); 3.7(t,2H); 5.6(s,1H); 7.0-7.2(m,5H); 7.2-7.4(m,1H); 10.6(br s,1H). Mass spectrum: 412 (M+1).

Part F:

2-Amino-1,4-dihydro-4-(2-{4-[4-(2-methoxyphenyl)-1-piperazinyl]-butylthio}phenyl)-6-methyl-5-nitro-3-pyridinecarboxylic acid methyl ester To a 5 liter 4-neck round-bottom flask fitted with mechanical stirrer, reflux condenser and thermowell, under a nitrogen atmosphere, was added 37.87 g of 2-amino- 1,4-dihydro-4-(2-[(4-chlorobutyl)thio]phenyl)-6-methyl-5-nitro-3-pyridinecarboxylic acid methyl ester, 3.5 liters of isopropanol, 35.35 g of 1-(2-methoxyphenyl)piperazine, 27.57 g of sodium iodide and 15.45 g of sodium bicarbonate. The reaction mixture was heated at reflux for 6.5 hr., then stirred overnight at room temperature. The solvent was removed by rotary evaporation and the residue was partitioned between dichloromethane and water. The aqueous layer was washed with dichloromethane (2×300 ml), the organic layers combined, washed with water, dried over magnesium sulfate, filtered and concentrated. The crude product was purified by column chromatography, eluting with 5% methanol in ethyl acetate. The product (Ex. No. 1, Table 1) was isolated as an orange solid, 37.23 g. $^1$H-NMR ($d_6$-DMSO) δ 1.60(m,4H); 2.33(m,2H); 2.40(s,3H); 2.45(m,4H); 2.92(m,6H); 3.43(s,3H); 3.76(s,3H); 5.59(s,1H); 6.73-6.95(m,6H); 7.09(m,2H); 7.35(m,1H); 9.50(br s,1H). Mass spectrum: 568 (M+1).

EXAMPLE 2

2-Amino-1,4-dihydro-4-(2-{4-[4-(2-methoxyphenyl)-1-piperazinyl]-butylsulfinyl}phenyl)-6-methyl-5-nitro-3-pyridinecarboxylic acid methyl ester To a 4-neck 500 ml round-bottom flask fitted with an addition funnel, thermometer and mechanical stirrer under a nitrogen atmosphere, was added 5.00 g of 2-amino-1,4-dihydro-4-(2-{4-[4-(2-methoxyphenyl)-1-piperazinyl]-butylthio}phenyl)-6-methyl-5-nitro-3-pyridinecarboxylic acid methyl ester and 120 ml of dichloromethane, followed by 1.73 ml of trifluoromethanesulfonic acid. The reaction mixture was cooled to −10° C. with an ice/acetone bath, and 1.88 g of 80% m-chloroperbenzoic acid in 120 ml of dichloromethane was added dropwise, maintaining −5° to −10° C. The reaction was stirred for an additional 2 hr. at −10° C. after the addition was complete. The reaction mixture was poured into conc. sodium bicarbonate, and the reaction flask was rinsed with acetone. The organic layer was separated, dried over magnesium sulfate, filtered and concentrated to an orange oil. The product (Ex. No. 2, Table 1) was isolated after column chromatography on silica gel, eluting with 20% methanol in ethyl acetate as an orange foam, 2.8 g. $^1$H-NMR ($CDCl_3$) δ 1.84-2.05(m,2H); 2.03-2.05(m,2H); 2.36(s,3H); 2.55(t,2H,J=7 Hz); 2.71(br s,4H); 3.00-3.18(br s,6H); 3.61(s,3H); 3.85(s,3H); 5.76(s,1H); 6.70(br s,2H); 6.83-7.03(m,4H); 7.28-7.41(m,4H); 7.82-7.86(m,1H). Mass spectrum: 584 (M+1).

EXAMPLE 3

Part A: 2-(5-Chloropentyloxy)benzaldehyde

To a solution of 100 g (0.82 mol) of salicylaldehyde in 2000 ml of iPrOH was added 228 g (1.23 mol) of 1-bromo-5-chloro-pentane, followed by 113 g (0.82 mol) of potassium carbonate. The reaction was refluxed under nitrogen and followed by TLC. After cooling to room temperature, the mixture was filtered and the filtrate was concentrated under reduced pressure to remove all solvent. The liquid residue was purified by fractional distillation under reduced pressure: 1st fraction: 45°-50° C., 0.4 mm Hg [$Br(CH_2)_5Cl$] 2nd fraction: 159.8 g (86% yield), 145°-150° C., 0.3 mm Hg colorless liquid product. The remaining residue proved to a dialdehyde by-product. TLC: Starting aldehyde Rf=0.46 (30% ether/pet. ether). Desired aldehyde: Rf=0.35. By-product: Rf=0.15.

Part B:

N-[2-(4-Chloropentyloxy)phenylmethylene]-1butanamine

To a 100 ml 3-neck round-bottom flask fitted with mechanical stirrer and thermowell, under a nitrogen atmosphere, was added 4.53 g of 2-(5-chloropentyloxy)-benzaldehyde and 20 ml of diethyl ether, followed by 12.0 g of magnesium sulfate, 1.46 g of N-butylamine, and 0.2 ml of concentrated sulfuric acid (added dropwise). The mixture was stirred at room temperature overnight. The solid was removed and the filtrate was concentrated to give the imine as an oil, 5.2 g. $^1$H-NMR ($CDCl_3$) δ 0.94(t,3H,J=7 Hz); 1.34-1.48(m,2H); 1.57-1.72(m,4H); 1.75-1.93(m,4H); 3.44-3.65(m,4H); 4.02(t,2H,J=6 Hz); 6.87(d,1H,J=6 Hz); 6.92(t,1H,J TM 8 Hz); 6.96(t,1H,J=7 Hz); 7.29-7.95(m,1H); 8.69(s,1H). IR: 1637 $cm^{-1}$.

Part C:

4-[2-(4-Chloropentyloxy)phenyl]-3-nitro-3-buten-2-one

To a 100 ml 3-neck round-bottom flask fitted with mechanical stirrer and thermowell, under a nitrogen atmosphere, was added 5.1 g of N-[2-(4-chloropentyloxy)phenylmethylene]-1-butanamine and 30 ml of benzene, followed by 10 ml of acetic anhydride. The mixture was cooled in an ice water bath as 1.87 g of nitroacetone was added. The bath was permitted to warm to room temperature, and the reaction stirred overnight. The solvent was removed by rotary evaporation, and the product was partitioned between ether and sodium bicarbonate. After drying over magnesium sulfate, the solvent was removed to give 6.6 g of the product, which was a mixture of the olefin and N-acetylbutylamine.

Part D:

2-Amino-1,4-dihydro-4-2-(4-chloropentyloxy)phenyl]-6-methyl-5-nitro-3-pyridinecarboxylic acid methyl ester To a 1-neck 100 ml round-bottom flask Containing 3.3 g of 4-[2-(4-chloropentyloxy)phenyl]-3-nitro-3-buten-2-one and a stir bar, under a nitrogen atmosphere, was added 20 ml of methanol. The solution was cooled in an ice bath as 1.52 g of amidino-acetic acid methyl ester hydrochloride and 2.3 ml of 25% sodium methoxide in methanol was added. An orange solid formed shortly. After stirring at room temperature overnight, the product was collected by filtration and washed with cold methanol then dried for 1 hr. under vacuum to give 0.19 g of the dihydropyridine as an orange solid. Mass spectrum: 410 (M+H).

Part E:
2-Amino-1,4-dihydro-4-(2-{5-4-(2-pyrimidinyl)-1-piperazinyl]-pentyloxy}phenyl)-6-methyl-5-nitro-3-pyridinecarboxylic acid methyl ester To a 100 ml 3-neck round-bottom flask fitted with mechanical stirrer, reflux condenser and thermowell, under a nitrogen atmosphere, was added 2.05 g of 2-amino-1,4-dihydro-4-[2-(4-chloropentyloxy)phenyl]-6-methyl-5-nitro-3-pyridinecarboxylic acid methyl ester, 40 ml of DMF, 1.20 g of 1-(2-pyrimidinyl)piperazine, 1.50 g of sodium iodide and 1.70 g of sodium bicarbonate. The reaction mixture was heated at 75° C. overnight. The solvent was removed by rotary evaporation, and the residue was partitioned between dichloromethane and water. The aqueous layer was washed with dichloromethane (2×300 ml), the organic layers combined, washed with water, dried over magnesium sulfate, filtered and concentrated. The crude product was purified by column chromatography and eluted with 5% methanol in ethyl acetate. The product (Ex. No. 3, Table 1) was isolated as an orange solid, 0.67 g, m.p. 164° C. (dec). $^1$H-NMR ($CDCl_3$) δ 1.43–1.79(m,6H); 2.35–2.53(m,8H); 2.47(s,3H); 3.56(s,3H); 3.80–3.93(m,5H); 5.35(s,1H); 6.47–6.52(m,3H}; 6.74–6.84(m,2H); 7.06–7.34(m,2H); 8.30(d,2H,J=5 Hz). Mass spectrum: 538 (M+H).

EXAMPLE 4

2-Amino-1,4-dihydro-4-(2-{5-[4-(2-methoxyphenyl)-1-piperazinyl]-pentyloxy}phenyl)-6-methyl-5-nitro-3-pyridinecarboxylic acid methyl ester This compound (m.p. 167° C.) was prepared from 2-amino-1,4-dihydro-4-[2-(4-chloropentyloxy)phenyl]-6-methyl-5-nitro-3-pyridinecarboxylic acid methyl ester and 2-methoxyphenyl-1-piperazine as described for Example 3. $^1$H-NMR ($CDCl_3$) δ 1.21–1.75(m,6H); 2.45(s,3H); 2.45–2.48(m,2H); 2.69(br s,4H); 3.10(br s,4H); 3.56(s,3H); 3.86(s,3H); 3.86–3.93(m,2H); 5.36(s,1H); 6.50(s,2H); 6.74–7.16(m,8H); 7.32(d,1H,J=6 Hz). Mass spectrum: 566 (M+H). IR: 3402,1689 $cm^{-1}$.

EXAMPLE 5

Part A: 2-[4-Chlorobutyl)sulfonyl]benzyl alcohol

To a solution of B.11 g of 2-(4-chlorobutyl)thio]benzyl alcohol in 100 ml of dichloromethane at 0° C. was added m-chloroperbenzoic acid (15.09 g of 80% in 150 ml of dichloromethane) dropwise. After addition was complete, the ice-bath was removed and the mixture was allowed to stir at room temperature overnight. The mixture was filtered and the filtrate was washed with aqueous sodium bicarbonate, dried over magnesium sulfate, and the solvent was evaporated to give the crude product, which was purified via column chromatography on silica gel, eluting with 60:25:15 toluene:ethyl acetate:methanol to give 4.5 g of pure product. $^1$H-NMR ($CDCl_3$) δ 1.81–2.02(m,4H); 3.24–3.35(m,2H); 3.50–3.56(t,2H,J=6 Hz); 4.94(s,2H); 7.49–7.71(m,3H); 7.95–8.06(m,1H). Mass spectrum: 263 (M+H).

Part B: 2-[(4-Chlorobutyl)sulfonyl]benzaldehyde 2.8 g of 2-[(4-chlorobutyl)sulfonyl]benzyl alcohol was treated with 1.4 ml of oxalyl chloride, 2.4 ml of dimethylsulfoxide, and 7.8 ml of triethylamine in the same manner as described for Example 1, Part B. Purification of the crude product via column chromatography on silica gel, eluting with 60:10:30 toluene:ethyl acetate:hexane provided 2.45 g of the product. $^1$H-NMR ($CDCl_3$) δ 1.91–1.97(m,4H); 3.35(t,2H,J=7 Hz); 3.54(t,2H,J=6 Hz); 7.80–7.85(m,2H); 8.07–8.14(m,2H); 10.75(s,1H). Mass spectrum: 261 (M+H).

Part C:
N-{2-[(4-Chlorobutyl)sulfonyl]phenylmethylene}-1-butanamine 2.45 g of 2-[(4-chlorobutyl)sulfonyl]benzaldehyde was treated with 1.1 ml of n-butylamine, 3.4 g of magnesium sulfate, and 2 drops of concentrated sulfuric acid in 20 ml of diethyl ether in the same manner as described for Example 1, Part C to give 2.76 g of product. $^1$H-NMR ($CDCl_3$) δ 0.96(t,3H,J=7 Hz); 1.32–1.50(m,2H); 1.65–1.79(m,2H); 1.84–1.93(m,4H); 3.11–3.20(m,2H); 3.46–3.53(m,2H); 3.67–3.74(m,2H); 7.55–7.73(m,2H); 8.00–8.13(m,2H); 9.12(s,1H).

Part D:
4-{2-[(4-Chlorobutyl)sulfonyl]phenyl}-3-nitro-3-buten-2-one

In a 100 ml flask under a nitrogen atmosphere at 0° C. was added 2.76 g of N-{2-[(4-chlorobutyl)sulfonyl]-phenylmethylene}-1-butanamine, 25 ml of acetic anhydride and 0.90 g of nitroacetone. The mixture was stirred at room temperature for 3 h., then partitioned between ether and saturated sodium bicarbonate solution. The ether layer was washed with saturated sodium chloride, dried over magnesium sulfate and evaporated to give 3.2 g of the product, as a 1:1 mixture with N-acetyl-n-butylamine.

Part E:
2-Amino-1,4-dihydro-4-{2-[(4-chlorobutyl)sulfonyl]-phenyl}-6-methyl-5-nitro-3-pyridinecarboxylic acid methyl ester To a solution of 3.2 g of 4-{2-[(4-chlorobutyl)sulfonyl]phenyl}-3-nitro-3-buten-2-one in 25 ml of methanol in a 100 ml single-neck flask at 0° C. was added 1.41 g of amidino-acetic acid methyl ester hydrochloride, followed by 2.2 ml of 25% sodium methoxide in methanol. The mixture was warmed to room temperature and stirred overnight. After removal of the methanol, the residue was partitioned between water and dichloromethane. The organic layer was dried over magnesium sulfate and evaporated to give a crude product, which was purified via column chromatography on silica gel, eluting with 60:40 toluene:ethyl acetate. Recrystallization from isopropyl acetate provided 1.08 g of an orange product, m.p. 218° C. $^1$H-NMR ($d_6$-DMSO) δ 1.71–1 95(m,4H); 2.45(s,3H); 2.48–2.55(m,2H); 3.34(s,3H); 3.69(m,2H); 6.49(s,1H); 6.87(br s,2H); 7.33–7.44(m,2H); 7.56(t,1H,J=8 Hz); 7.79(d,1H,J=8 Hz); 9.51(br s,1H). Mass spectrum: 444 (M+H).

Part F:
2-Amino-1,4-dihydro-4-(2-{4-[4-(2-methoxyphenyl)-1-piperazinyl]-butylsulfonyl}phenyl)-6-methyl-5-nitro-3-pyridinecarboxylic acid methyl ester 0.89 g of 2-amino-1,4-dihydro-4-{2-[(4-chlorobutyl)-sulfonyl]phenyl}-6-methyl-5-nitro-3-pyridinecarboxylic acid methyl ester was treated with 0.60 g of sodium iodide, 0.34 g of sodium bicarbonate and 0.42 g of 2-methoxyphenyl-1-piperazine in 25 ml of DMF using the procedure as described for Example 3. Purification via column chromatography on silica gel, eluting with 60:35:5 toluene:ethyl acetate:methanol gave 0.10 g of product, m.p. 145°-147° C. $^1$H-NMR ($d_6$-DMSO) δ 1.57-1.63(m,2H); 1.80-1.87(m,2H); 2.36(t,2H,J=7 Hz); 2.45(s,3H); 2.49(s,4H); 2.94(s,4H); 3.35(m,2H); 3.40(s,3H); 3.77(s,3H); 6.50(s,1H); 6.88-6.92(m,6H); 7.35-7.81(m,4H); 9.50(br s,1H). Mass spectrum: 600 (M+H).

EXAMPLE 8

2-Amino-1,4-dihydro-4-(2-{4-[4-(2-pyrimidinyl)-1-piperazinyl]-butylsulfinyl}phenyl)-6-methyl-5-nitro-3-pyridinecarboxylic acid methyl ester This compound was prepared from 2-amino-1,4-dihydro-4-(2-{4-[4-(2-methoxyphenyl)-1-piperazinyl]-butylthio)phenyl)-6-methyl-5-nitro-3-pyridinecarboxylic acid methyl ester and m-chloroperbenzoic acid in the same manner as described for Example 2. $^1$H-NMR ($CDCl_3$) δ 1.82-1.88(m,2H); 2.03-2.06(m,2H); 2 40(s,3H); 2.45-2.52(m,6H); 3.00-3.15(m,2H); 3.61(s,3H); 3.83(br s,4H); 5.76(s,1H); 6.44-6.49(m,1H); 6.70(br s,2H); 7.15-7.39(m,4H); 7.81-7.84(m,1H); 8.28-8.30(m,2H).

EXAMPLE 13

2-Amino-1,4-dihydro-4-(2-{4-[4-(2-methoxyphenyl)-1-piperazinyl]-pentylsulfinyl}phenyl)-6-methyl-5-nitro-3-pyridinecarboxylic acid methyl ester This compound was prepared from 2-amino-1 4-dihydro-4-(2-{4-[4-(2-methoxyphenyl)-1-piperazinyl]-pentylthio}phenyl)-6-methyl-5-nitro-3-pyridinecarboxylic acid methyl ester and m-chloroperbenzoic acid in the same manner as described for Example 2. $^1$H-NMR ($CDCl_3$) δ 1.65(br s,4H); 2.02(m,2H); 2.42(s,3H); 2.49(m,2H); 2.71(s,4H); 2.98(m,2H); 3.12(s,4H); 3.61(s,3H); 3.86(s,3H); 5.76(s,1H); 6.68(s,2H); 6.84-7.01(m,4H); 7.27(m,4H); 7.81-7.86(m,1H). Mass spectrum: 598 (M+H).

Other compounds which can or were prepared by such procedures and procedures described in the synthetic disclosure are illustrated by the structures represented in Tables 1 and 2. These Tables are intended to illustrate the invention, but not limit its breadth.

TABLE 1

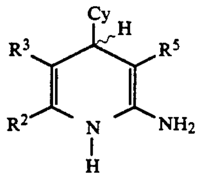

(I)

| Ex. No. | Cy | $R^2$ | $R^3$ | $R^5$ | mp °C. |
|---|---|---|---|---|---|
| 1 | 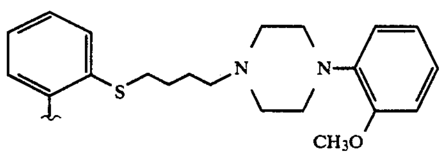 | $CH_3$ | $NO_2$ | $CO_2CH_3$ | glassy solid[a] |
| 2 | 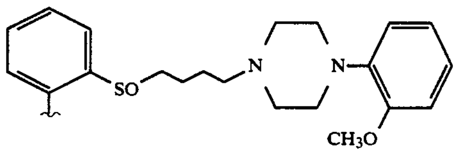 | $CH_3$ | $NO_2$ | $CO_2CH_3$ | glassy solid[b] |
| 3 | 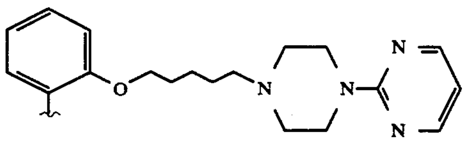 | $CH_3$ | $NO_2$ | $CO_2CH_3$ | 164[c] (dec) |
| 4 | 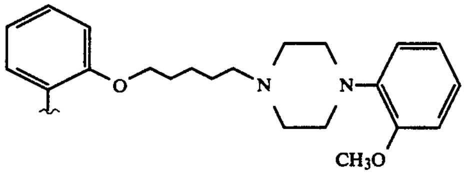 | $CH_3$ | $NO_2$ | $CO_2CH_3$ | 167[d] (dec) |
| 5 | 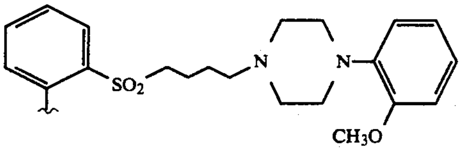 | $CH_3$ | $NO_2$ | $CO_2CH_3$ | 145-7[e] |

TABLE 1-continued
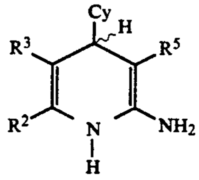
(I)
| Ex. No. | Cy | $R^2$ | $R^3$ | $R^5$ | mp °C. |
|---|---|---|---|---|---|
| 6 | 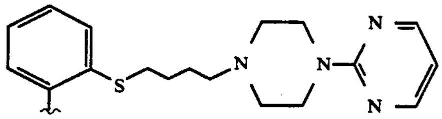 | $CH_3$ | $NO_2$ | $CO_2CH_3$ | glassy solid[f] |
| 7 | 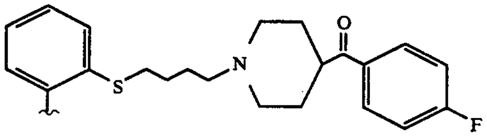 | $CH_3$ | $NO_2$ | $CO_2CH_3$ | glassy solid[g] |
| 8 | 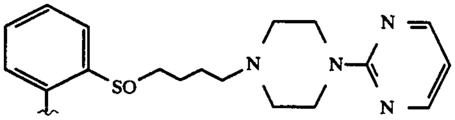 | $CH_3$ | $NO_2$ | $CO_2CH_3$ | glassy solid[h] |
| 9 | 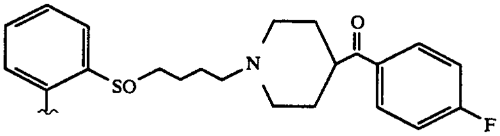 | $CH_3$ | $NO_2$ | $CO_2CH_3$ | 138-142[i] |
| 10 | 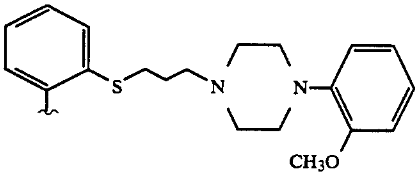 | $CH_3$ | $NO_2$ | $CO_2CH_3$ | glassy solid[j] |
| 11 | 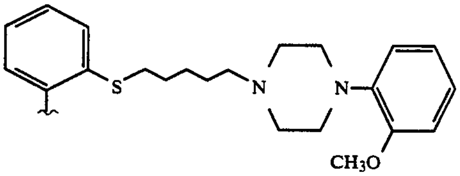 | $CH_3$ | $NO_2$ | $CO_2CH_3$ | glassy solid[k] |
| 12 | 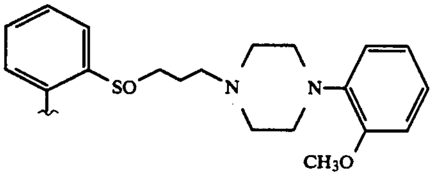 | $CH_3$ | $NO_2$ | $CO_2CH_3$ | 226[l] |
| 13 | 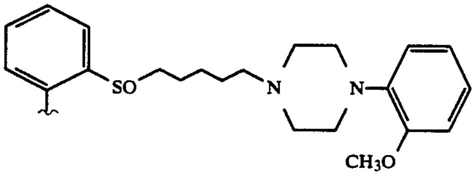 | $CH_3$ | $NO_2$ | $CO_2CH_3$ | 206[m] (dec) |

TABLE 1-continued
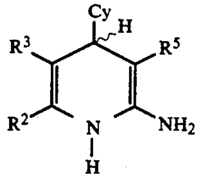
(I)
| Ex. No. | Cy | $R^2$ | $R^3$ | $R^5$ | mp °C. |
|---|---|---|---|---|---|
| 14 | 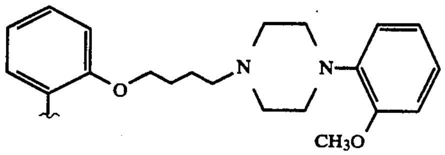 | $CH_3$ | $NO_2$ | $CO_2CH_3$ | |
| 15 | 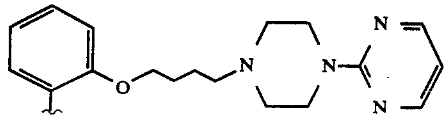 | $CH_3$ | $NO_2$ | $CO_2CH_3$ | |
| 16 | 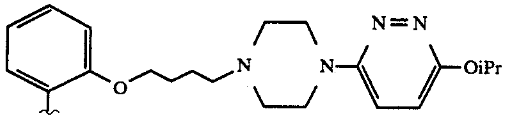 | $CH_3$ | $NO_2$ | $CO_2CH_3$ | |
| 17 | 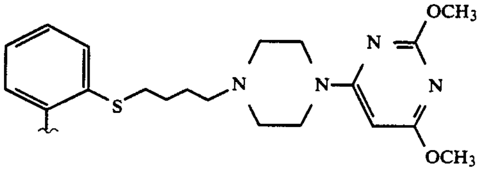 | $CH_3$ | $NO_2$ | $CO_2CH_3$ | |
| 18 | 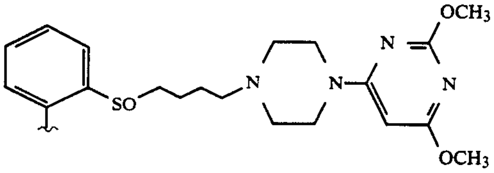 | $CH_3$ | $NO_2$ | $CO_2CH_3$ | |
| 19 | 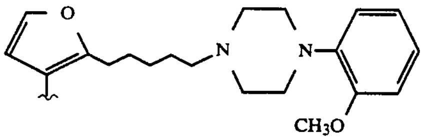 | $CH_3$ | $NO_2$ | $CO_2CH_5$ | |
| 20 | 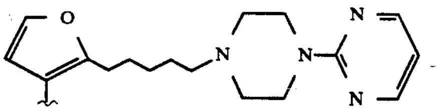 | 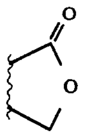 | | $CO_2CH_3$ | |
| 21 | 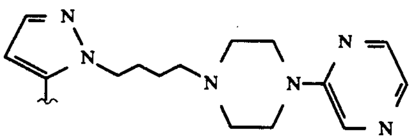 | $CH_3$ | $NO_2$ | $COCH_3$ | |
| 22 | 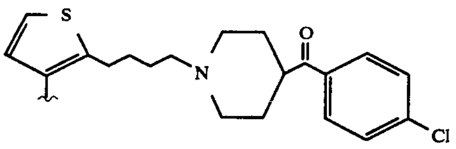 | $C_2H_5$ | $NO_2$ | $CO_2CH_3$ | |

TABLE 1-continued
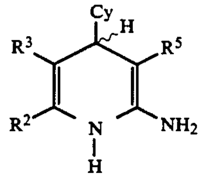
(I)
| Ex. No. | Cy | $R^2$ | $R^3$ | $R^5$ | mp °C. |
|---|---|---|---|---|---|
| 23 | 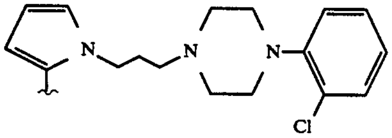 | $CH_3$ | $NO_2$ | $CO_2CH_2CHOHC_6H_5$ | |
| 24 | 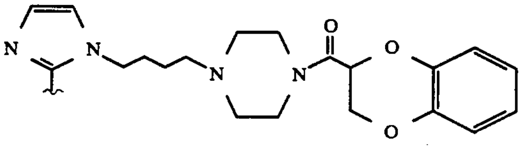 | $CH_3$ | $NO_2$ | $NO_2$ | |
| 25 | 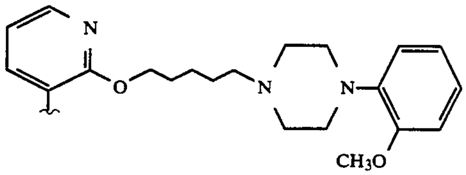 | $CH_3$ | $NO_2$ | $CO_2CH_3$ | |
| 26 | 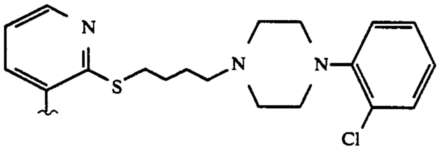 | $CH_3$ | $NO_2$ | $CO_2C_3H_7$ | |
| 27 | 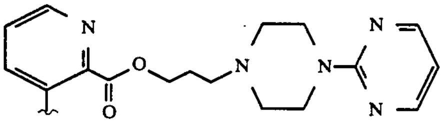 | 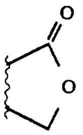 | | $CONHC_6H_5$ | |
| 28 | 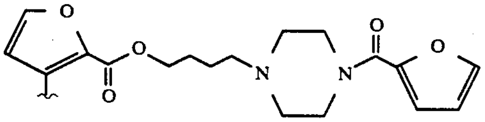 | $CH_3$ | $NO_2$ | CHO | |
| 29 | 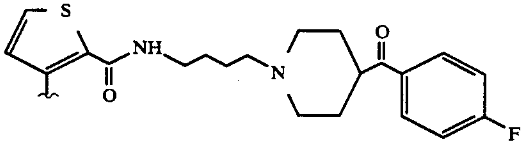 | $CH_3$ | CN | $CO_2CH_3$ | |
| 30 | 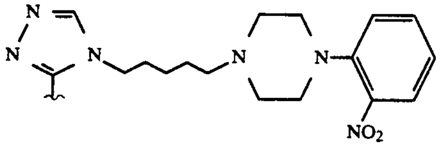 | $CH_3$ | $NO_2$ | $CO_2CH_3$ | |
| 31 | 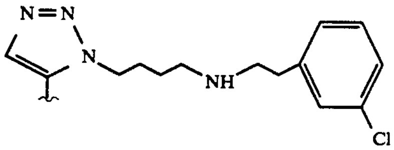 | $C_3H_7$ | $NO_2$ | $CO_2CH_3$ | |

TABLE 1-continued
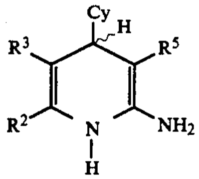
(I)
| Ex. No. | Cy | $R^2$ | $R^3$ | $R^5$ | mp °C. |
|---|---|---|---|---|---|
| 32 | 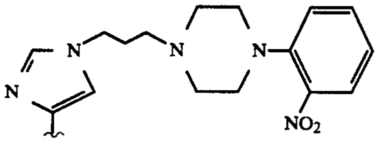 | $CH_3$ | $NO_2$ | $CO_2CH_3$ | |
| 33 | 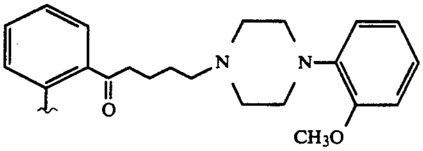 | $CH_3$ | $NO_2$ | $CO_2CH_3$ | |
| 34 | 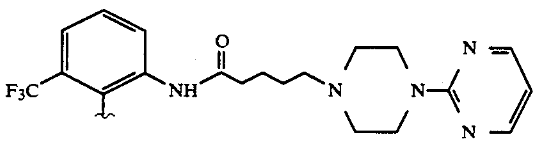 | 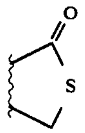 | | $CO_2CH_3$ | |
| 35 | 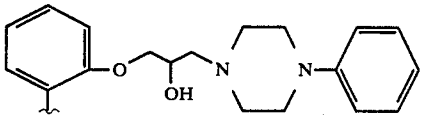 | $CH_3$ | $NO_2$ | $CO_2C_2H_5$ | |
| 36 | 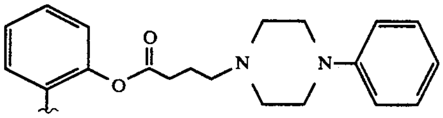 | $CH_3$ | $NO_2$ | $CO_2C_4H_9$ | |
| 37 | 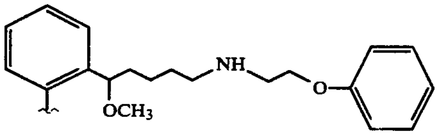 | $CH_3$ | $NO_2$ | $COCH_3$ | |
| 38 | 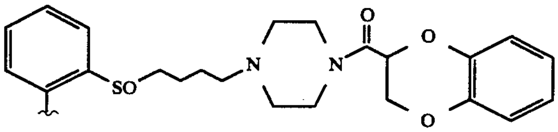 | $CH_3$ | $NO_2$ | $CO_2CH_3$ | |
| 39 | 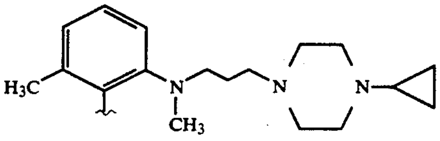 | $CH_3$ | $NO_2$ | $CO_2C_2H_5$ | |

TABLE 1-continued
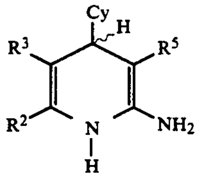
(I)
| Ex. No. | Cy | $R^2$ | $R^3$ | $R^5$ | mp °C. |
|---|---|---|---|---|---|
| 40 | 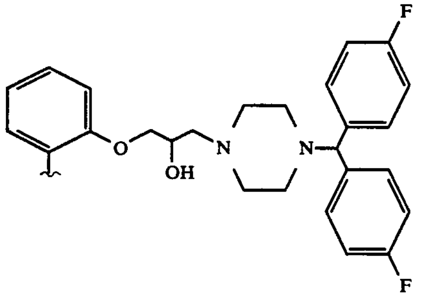 | 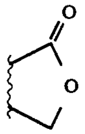 | | $CO_2CH_3$ | |
| 41 | 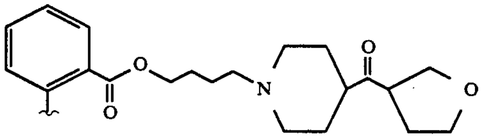 | $CH_3$ | CN | $CO_2CH_3$ | |
| 42 | 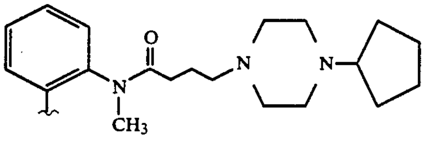 | $CH_3$ | $CONH_2$ | $CO_2CH_3$ | |
| 43 | 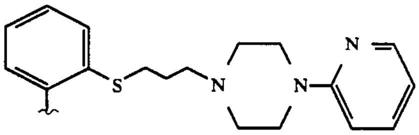 | $CH_3$ | $NO_2$ | $CO_2CH_3$ | |
| 44 | 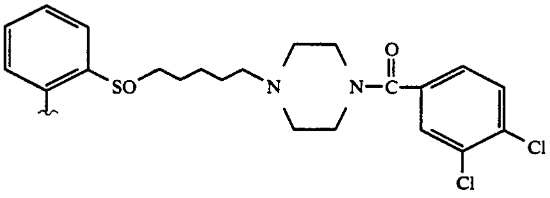 | $CH_3$ | $NO_2$ | $NO_2$ | |
| 45 | 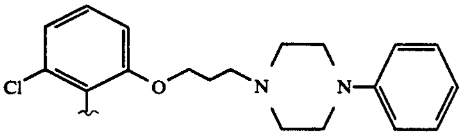 | $NH_2$ | $CONH_2$ | $CO_2CH_3$ | |
| 46 | 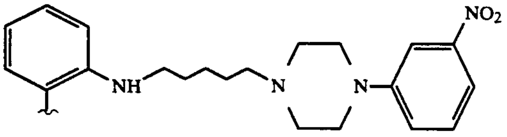 | $CH_2OH$ | CN | $CO_2CH_3$ | |
| 47 | 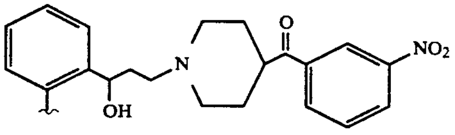 | $NH_2$ | H | $CO_2CH_3$ | |

TABLE 1-continued

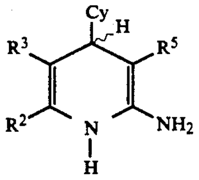

(I)

| Ex. No. | Cy | $R^2$ | $R^3$ | $R^5$ | mp °C. |
|---|---|---|---|---|---|
| 48 | 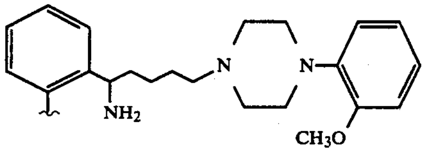 | $CH_3$ | $NO_2$ | $CO_2C_2H_5$ | |
| 49 | 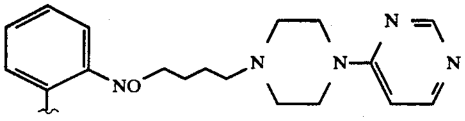 | $C_2H_5$ | $NO_2$ | $CO_2CH_3$ | |
| 50 | 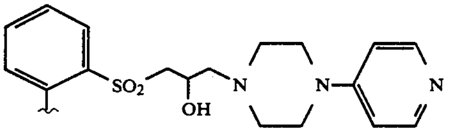 | $C_3H_7$ | $NO_2$ | $CO_2C_2H_5$ | |

[a]See text for spectral data.
[b]See text for spectral data.
[c]See text for spectral data.
[d]See text for spectral data.
[e]See text for spectral data.
[f]NMR: ($CDCl_3$) ∂ 1.70–1.73(m, 4H); 2.41–2.54(m, 7H); 2.96–3.01(m, 4H); 3.59(s, 3H); 3.82(t, 4H, J=5Hz); 5.73(s, 1H); 6.49(t, 3H, J=5Hz); 7.07–7.33(m, 5H); 8.30(d, 2H, J=5Hz). Mass Spec: 540(M+H).
[g]NMR: ($CDCl_3$) ∂ 1.67(m, 4H); 1.83(m, 4H); 2.13(m, 2H); 2.40(m, 2H); 2.47(s, 3H); 2.98(m, 4H); 3.20(m, 1H); 3.57(s, 3H); 5.70(s, 1H); 6.53(s, 2H); 7.05–7.35(m, 7H); 7.90–8.05(m, 2H). Mass Spec: 583(M+H).
[h]See text for spectral data.
[i]NMR: ($d_6$-DMSO) ∂ 1.55–1.72(m, 4H); 1.72–1.90(m, 4H); 2.13(m, 2H); 2.42(m, 2H); 2.52(s, 3H); 2.83(m, 2H); 2.94(d, 2H, J=11Hz); 3.40(m, 1H); 3.49(s, 3H); 5.60(s, 1H); 7.09(br s, 2H); 7.26(dd, 1H, J=1, 7Hz); 7.30–7.53(m, 4H); 7.82(dd, 1H, J=1, 7Hz); 8.07(dd, 2H, J=6, 8Hz). IR(KBr): 3420, 3308, 2946, 1684, 1646, 1598, 1562, 1495, 1470, 1438, 1384, 1300, 1251, 1189, 1157, 1125, 1065, 996 $cm^{-1}$ Mass Spec: 599(M+H), 320, 262.
[j]NMR: ($CDCl_3$) ∂ 1.89–2.05(m, 2H); 2.46(s, 3H); 2.59(t, 2H, J=7Hz); 2.68(s, 4H); 2.94–2.99(m, 2H); 2.99(s, 4H); 3.59(s, 3H); 3.86(s, 3H); 5.77(s, 1H); 6.56(s, 2H); 6.84–7.38(m, 8H); 8.03(s, 1H). Mass Spec: 554(M+H).
[k]NMR: ($CDCl_3$) ∂ 1.40–1.65(m, 4H); 1.65–1.85(m, 2H); 2.36–2.46(m, 2H); 2.46(s, 3H); 2.68(br s, 4H); 2.94(m, 2H); 3.11(br s, 4H); 3.59(s, 3H); 3.86(s, 3H); 5.78(s, 1H); 6.55(s, 2H); 6.88–7.31(m, 8H); 8.03(s, 1H). Mass Spec: 582(M+H).
[l]NMR: ($CDCl_3$) ∂2.20–2.30(m, 2H); 2.38(s, 3H); 2.72(br s, 6H); 2.72–3.30(m, 6H); 3.60(s, 3H); 3.85(s, 3H); 5.78(s, 1H); 6.73(br s, 2H); 6.83–7.04(m, 4H); 7.15–7.45(m, 3H); 7.82–7.86(m, 1H); 9.20(br s, 1H). Mass Spec: 570(M+H).
[m]See text for spectral data.

TABLE 2

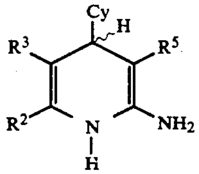

(I)

| Ex. No. | Cy | $R^2$ | $R^3$ | $R^5$ |
|---|---|---|---|---|
| 51 | 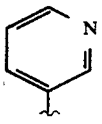 | $CH_3$ | $NO_2$ | 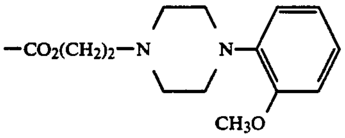 |
| 52 | 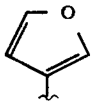 | $CH_3$ | $NO_2$ | 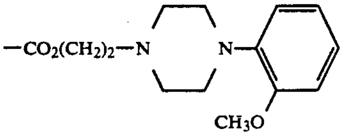 |

TABLE 2-continued
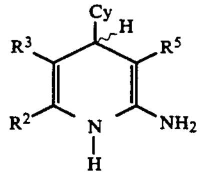
(I)
| Ex. No. | Cy | $R^2$ | $R^3$ | $R^5$ |
|---|---|---|---|---|
| 53 | 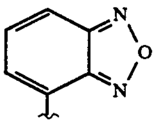 | $CH_3$ | $NO_2$ | 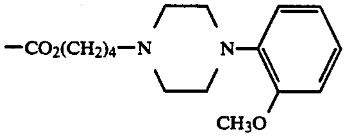 |
| 54 | 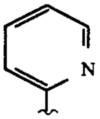 | $CH_3$ | $NO_2$ | 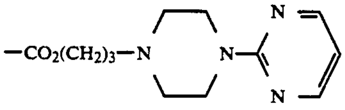 |
| 55 | 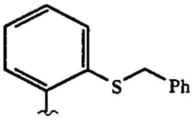 | $CH_3$ | $NO_2$ | 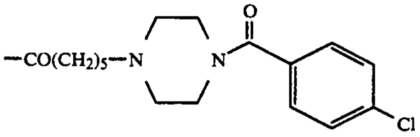 |
| 56 | 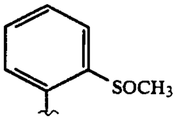 | 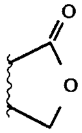 | | 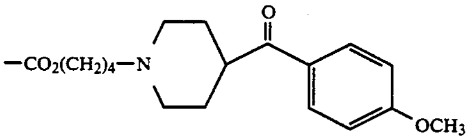 |
| 57 | 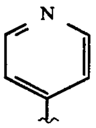 | $CH_2OH$ | $NO_2$ | 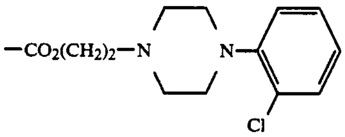 |
| 58 | 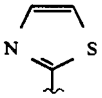 | $CH_3$ | $NO_2$ | 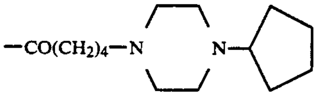 |
| 59 | 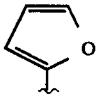 | $C_2H_5$ | $NO_2$ | 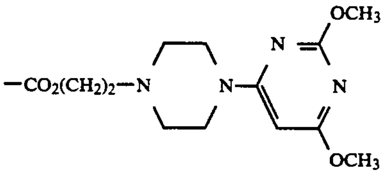 |
| 60 | 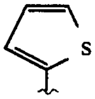 | $CH_3$ | $NO_2$ | 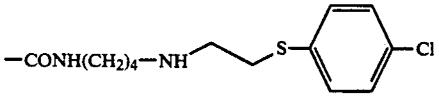 |
| 61 | 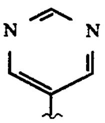 | 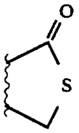 | | 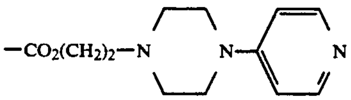 |

TABLE 2-continued
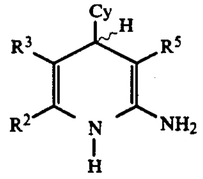
(I)
| Ex. No. | Cy | $R^2$ | $R^3$ | $R^5$ |
| --- | --- | --- | --- | --- |
| 62 | 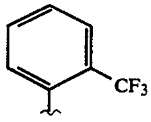 | $CH_3$ | CN | 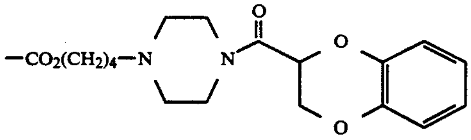 |
| 63 | 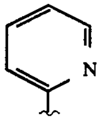 | $C_2H_5$ | $CONH_2$ | 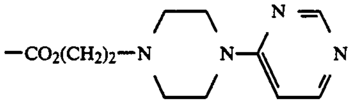 |
| 64 | 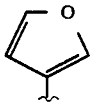 | $CH_3$ | $NO_2$ | 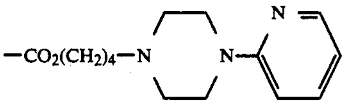 |
| 65 | 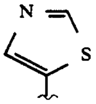 | $CH_3$ | $NO_2$ | 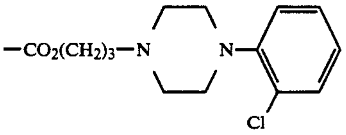 |
| 66 | 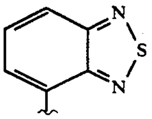 | $CH_2OH$ | CN | 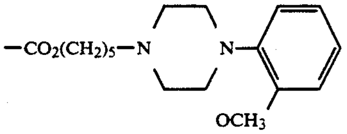 |
| 67 | 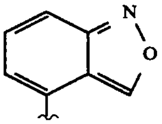 | $NH_2$ | H | 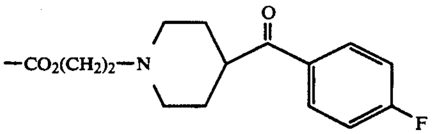 |
| 68 | 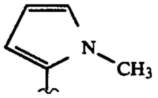 | $CH_3$ | $NO_2$ | 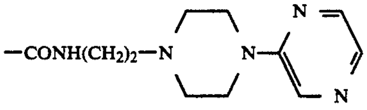 |
| 69 | 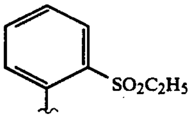 | $CH_3$ | $CONH_2$ | 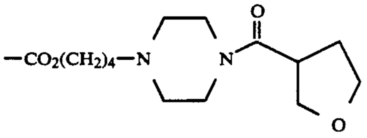 |

TABLE 2-continued

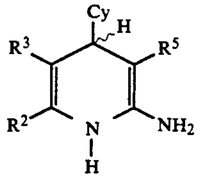

(I)

| Ex. No. | Cy | $R^2$ | $R^3$ | $R^5$ |
|---|---|---|---|---|
| 70 | 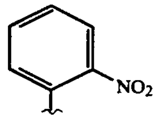 | $CH_3$ | $NO_2$ | 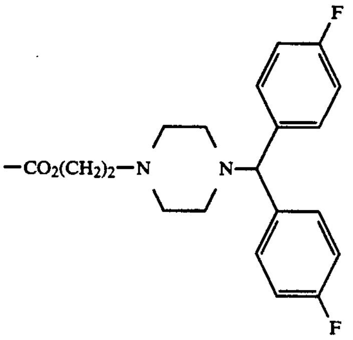 |
| 71 | 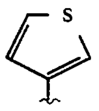 | 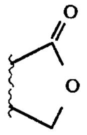 | | 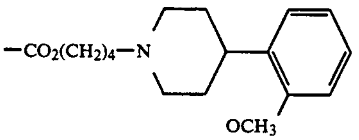 |
| 72 | 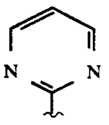 | 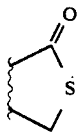 | | 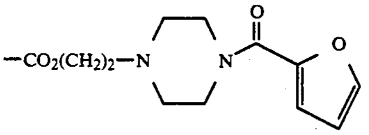 |
| 73 | 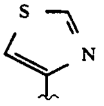 | CN | $CONH_2$ | 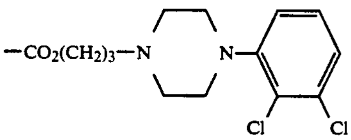 |
| 74 | 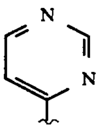 | $NH_2$ | $NO_2$ | 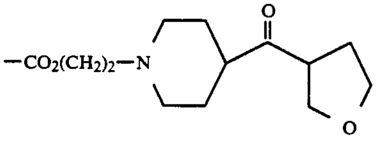 |
| 75 | 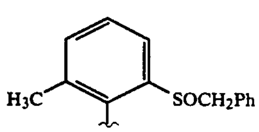 | 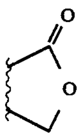 | | 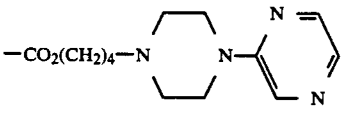 |

UTILITY

The compounds of this invention have been found to possess both $Ca^{2+}$ channel activity, preferably $Ca^{2+}$ agonist activity, and $alpha_1$-antagonist activity. These pharmacological properties of the compounds of this invention were evaluated in the following pharmacological experiments.

DETERMINATION OF AFFINITY FOR $ALPHA_1$-ADRENOCEPTORS

The $[^3H]$-prazosin binding assay was carried out according to the method described by Timmermans, P. B. M. W. M., Schoop, A. M. C., and Van Zwieten, P. A., *Biochem. Pharmacol.* 31, 899-905 (1982). The reaction mixture contained partially purified rat brain membranes (source of $alpha_1$-adrenoceptors), 0.2 nM $[^3H]$-prazosin with or without potential displacer in Tris buffer. The mixture was incubated for 60 minutes at 25° and subsequently terminated by rapid filtration through glass fiber-filter. Receptor-bound $[^3H]$-prazosin trapped in the filter was quantitated by scintillation counting. The inhibitory concentration ($IC_{50}$) of potential displacer which gives 50% displacement of the total specifically bound $[^3H]$-prazosin is presented as a measure of the affinity of such compound for the $alpha_1$-adrenoceptor.

DETERMINATION OF AFFINITY FOR CALCIUM CHANNELS

[$^3$H]-Nitrendipine binding assay was carried out according to the method described by G. T. Bolger, et al., *Biochem. Biophys. Res. Comm.* 104, 1604–1609 (1982). The reaction mixture contained rat cardiac microsomes (source of $Ca^{2+}$ channels), 0.5 nM [$^3$H]-nitrendipine with or without potential displacer in Tris buffer. The mixture was incubated for 60 minutes at 25° and subsequently terminated by rapid filtration through a glass fiber-filter. Membrane-bound [$^3$H]-nitrendipine trapped in the filter was quantitated by scintillation counting. The inhibitory concentration ($IC_{50}$) of potential displacer which gives 50% displacement of the total specifically bound [$^3$H]-nitrendipine is presented as a measure of the affinity of such compound for the $Ca^{2+}$ channel.

The results from the above two in vitro assays are summarized in Table 3.

TABLE 3

| | Binding Affinity Data for Calcium and $Alpha_1$ Adrenoceptors | |
|---|---|---|
| Ex. No. | [$^3$H]-Nitrendipine binding $IC_{50}$ [M] | [$^3$H]-Prazosin binding $IC_{50}$ [M] |
| 1 | $5.2 \times 10^{-7}$ | $6.0 \times 10^{-8}$ |
| 2 | $1.7 \times 10^{-6}$ | $1.1 \times 10^{-8}$ |
| 3 | $9.3 \times 10^{-7}$ | $1.6 \times 10^{-7}$ |
| 4 | $1.6 \times 10^{-6}$ | $3.4 \times 10^{-6}$ |
| 5 | $3.9 \times 10^{-7}$ | $6.0 \times 10^{-8}$ |
| 6 | $4.0 \times 10^{-7}$ | $4.5 \times 10^{-6}$ |
| 7 | $1.5 \times 10^{-7}$ | $1.5 \times 10^{-7}$ |
| 8 | $2.3 \times 10^{-6}$ | $2.4 \times 10^{-6}$ |
| 9 | $2.4 \times 10^{-6}$ | $1.5 \times 10^{-7}$ |
| 10 | $3.0 \times 10^{-7}$ | $8.0 \times 10^{-8}$ |
| 11 | $2.4 \times 10^{-7}$ | $4.2 \times 10^{-8}$ |
| 12 | $6.2 \times 10^{-7}$ | $5.2 \times 10^{-8}$ |
| 13 | $1.3 \times 10^{-6}$ | $2.5 \times 10^{-8}$ |

PROTOCOL FOR POSITIVE INOTROPIC EFFECT IN GUINEA PIG LEFT ATRIA

Guinea pigs are killed by cervical dislocation. The left atria are removed and mounted at 1 gm resting tension in tissue baths containing oxygenated Krebs bicarbonate solution which is kept at 37°. The left atria are electrically paced at 2 Hz with square wave pulses of 1 msec duration. The voltage is set at 1.5× threshold level.

After a one hour equilibration period, control values for developed tension (DT, gm) are recorded. Test compounds are then added to the baths, in a cumulative manner to a maximum concentration of $10^{-4}$, to obtain a concentration-response curve. Treatment values of DT are obtained after the drug effect has reached a plateau and the exposure time for each concentration is 5–8 minutes. Percent change of the treatment value from the control value is calculated at each concentration of the test compound. The results are shown in Table 4 below.

TABLE 4

| Ex. No. | $EC_{50}$ (M)[a] | Intrinsic Activity[b] |
|---|---|---|
| Control-Bay K8644 | $1.5 \times 10^{-7}$ | 100 |
| 1 | $5.5 \times 10^{-7}$ | 166 |
| 2 | $5.7 \times 10^{-6}$ | 90 |
| 3 | $1.0 \times 10^{-6}$ | 170 |
| 4 | $1.6 \times 10^{-6}$ | 128 |
| 5 | $1.5 \times 10^{-6}$ | 119 |
| 6 | $4.7 \times 10^{-8}$ | 113 |
| 7 | $9.6 \times 10^{-6}$ | 112 |
| 8 | $5.0 \times 10^{-7}$ | 254 |
| 9 | $1.0 \times 10^{-5}$ | 56 |
| 10 | $3.5 \times 10^{-6}$ | 115 |
| 11 | $2.4 \times 10^{-6}$ | 112 |
| 12 | $>1.0 \times 10^{-4}$ | 35 |
| 13 | $5.2 \times 10^{-6}$ | 119 |

[a]$EC_{50}$ (M) = concentration that increases DT by 50% above the control DT.
[b]Intrinsic Activity is a ratio of the maximum effect of the test compound to that of Bay K8644 and expressed in percent.

The foregoing test results suggest that compounds of this invention have utility in the treatment of congestive heart failure.

DOSAGE FORMS

Compound of this invention can be administered to treat said deficiencies by any means that produces contact of the active agent with the agent's site of action in the body of the mammal. The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending on the use and known factors such as the pharmacodynamic characteristics of the particular agent, and its mode and route of administration; age, health, and weight of the recipient; nature and extent of symptoms, kind of concurrent treatment, frequency of treatment, and the effect desired. For use in the treatment of said diseases, a daily dosage of active ingredient can be about 50to 1000 mg.

Dosage forms (compositions) suitable for administration contain about 1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions or parenterally, in sterile liquid dosage forms. Alternatively it can be administered sublingually by tablets, gels, pastes, patches or lozenges.

Gelatin capsules contain the active ingredient and powdered carriers, such as lactose, starch, cellulose derivatives, magnesium stearate, stearic acid, and the like. Similar diluents can be used to make compressed tablets. Both tablets can be sugar coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl or propyl-paraben, and chlorobutanol. Suitable pharmaceutical carriers are described in *Remington's Pharmaceutical Sciences,* A. Osol, 17th Ed. (1985) a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredients, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium benzoate, 1.0 grams of sorbitol solution, U.S.P., and 0.025 milliliters of vanillin.

What is claimed is:

1. A compound of the formula

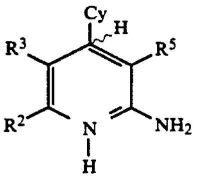

(I)

or a pharmaceutically acceptable salt thereof or an isomer or N-oxide thereof wherein:

$R^2$ is alkyl of 1-4 carbon atoms, CN, $CH_2OH$, $CH_2OCH_2CH_2NH_2$ or $NH_2$;

$R^3$ is $NO_2$, H, CN, $CONH_2$ or $R^2$ and $R^3$ taken together are:

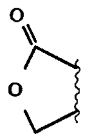
or
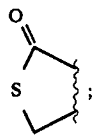
;

Cy, when $R^5$ is CHO, $CO_2CH_2CHOHC_6H_5$, $CO_2CH(OCH_3)C_6H_5$, $NO_2$, $CONHC_6H_5$, or $CO_2$ alkyl of 1-10 carbon atoms, is a cyclic group selected from the group:

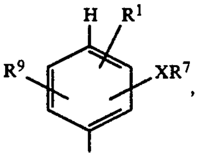
,
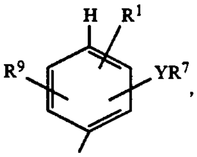
,
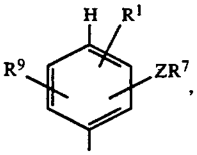
, $R^1$ and $R^9$ independently are H, alkyl of 1-4 carbon atoms, haloalkyl of 1-4 carbon atoms, alkoxy of 1-10 carbon atoms, halogen, or $NO_2$; Cy, when $R^5$ is $COR^7$, $CO_2R^7$ is phenyl optionally substituted with one or two substituents independently selected from the group consisting of alkyl of 1-4 carbon atoms, haloalkyl of 1-4 carbon atoms, alkoxy of 1-4 carbon atoms, thioalkyl of 1-4 carbon atoms, alkylsulfinyl of 1-4 carbon atoms, alkylsulfinyl of 1-4 carbon atoms, halogen, or $NO_2$, X is $NR^4$, O, S, SO, $SO_2$ or N→O;

Y is $CH_2$

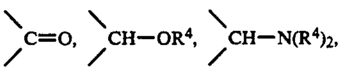

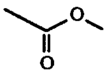
or
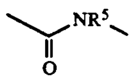
;

Z is

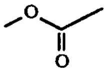
or
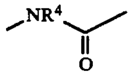

where $R^4$ is H or an alkyl group of 1-4 carbon atoms;

$R^7$ is

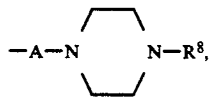

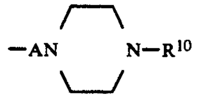

$R^{10}$ is

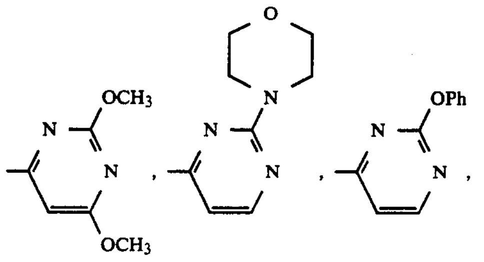

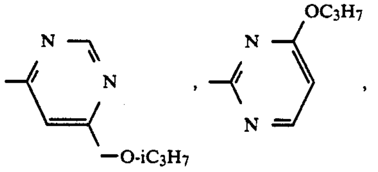

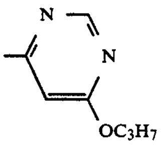

or 4-pyrimidinyl, $R^8$ is Ar,

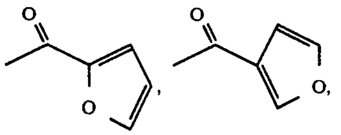

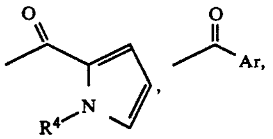

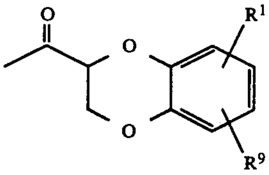

where

Ar is phenyl optionally substituted with one or two substituents independently selected from the group consisting of alkyl of 1–4 carbon atoms, haloalkyl of 1–4 carbon atoms, alkoxy of 1–4 carbon atoms, halogen, or $NO_2$;

Q is $(CH_2)_q$, $(CH_2)_nO$, $(CH_2)_nNH$ or $(CH_2)_nS$;

n is independently 1 to 4;

q is 0 to 2; and r is 1 to 10 with the proviso that when $R^2$ is alkyl of 1–4 carbon atoms, CN, $CH_2OH$, $CH_2OCH_2CH_2NH_2$ or $NH_2$; $R^3$ is $NO_2$, H, CN, $CONH_2$, then $R^8$ cannot be:

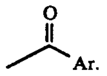

2. A compound of claim 1 wherein $R^2$ is $CH_3$.

3. A compound of claim 1 wherein $R^3$ is $NO_2$.

4. A compound of claim 1 where Cy is

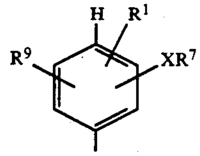

when $R^5$ is an alkyl ester of 1–4 carbon atoms; where $R^1$ and $R^9$ are H; X is O, S, SO, or $SO_2$;

$R^7$ is

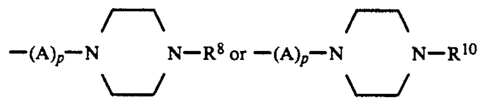

where

A is $CH_2$ and p is 2 to 5;

$R^8$ is Ar or

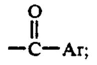

where

Ar is phenyl optionally monosubstituted with $OCH_3$, $CH_3$, or Cl; and $R^{10}$ is 2- or 4-pyrimidinyl.

5. A compound of claim 1 wherein:

$R^2$ is $CH_3$;

$R^3$ is $NO_2$; and

Cy is

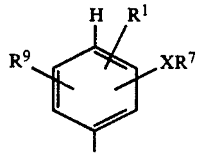

when $R^5$ is an alkyl ester of 1–4 carbon atoms; where $R^1$ and $R^9$ are H; X is O, S, SO, or $SO_2$;

$R^7$ is

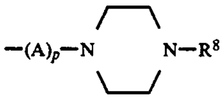 or 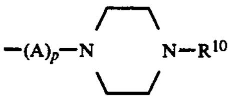

where

A is $CH_2$ and p is 2 to 5;

$R^8$ is Ar or

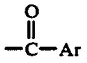

where

Ar is phenyl optionally substituted with $OCH_3$, $CH_3$, or Cl; and $R^{10}$ is 2- or 4-pyrimidinyl.

6. The compound of claim 1 which is 2-amino-1,4-dihydro-4-(2-{5-[4-(2-pyrimidinyl)-1-piperazinyl]-pentyloxy}phenyl)-6-methyl-5-nitro-3-pyridinecarboxylic acid methyl ester.

7. The compound of claim 1 which is 2-amino-1,4-dihydro-4-(2-{5-[4-(2-methoxyphenyl)-1-piperazinyl]-pentyloxy}phenyl)-6-methyl-5-nitro-3-pyridinecarboxylic acid methyl ester.

8. The compound of claim 1 which is 2-amino-1,4-dihydro-4-(2-{4-[4-(2-methoxyphenyl)-1-piperazinyl]-butylthio}phenyl)-6-methyl-5-nitro-3-pyridinecarboxylic acid methyl ester.

9. The compound of claim 1 which is 2-amino-1,4-dihydro-4-(2-{4-[4-(2-pyrimidinyl)-1-piperazinyl]-butylsulfinyl}phenyl)-6-methyl-5-nitro-3-pyridinecarboxylic acid methyl ester.

10. The compound of claim 1 which is 2-amino-1,4-dihydro-4-(2-{4-[4-(2-methoxyphenyl)-1-piperazinyl]-pentylsulfinyl}phenyl)-6-methyl-5-nitro-3-pyridinecarboxylic acid methyl ester.

11. A pharmaceutical composition comprising a pharmaceutically acceptable carrier and an effective amount of the compound of claim 6.

12. A pharmaceutical composition comprising a pharmaceutically acceptable carrier and an effective amount of the compound of claim 11.

* * * * *